US00PP13041P2

(12) United States Plant Patent
Kent

(10) Patent No.: US PP13,041 P2
(45) Date of Patent: Oct. 1, 2002

(54) GUZMANIA PLANT NAMED 'GUZ 230'

(75) Inventor: Jeffrey C. Kent, Encinitas, CA (US)

(73) Assignee: Ken't Bromeliad Nursery, Inc., Vista, CA (US)

( * ) Notice: Subject to any disclaimer, the term of this patent is extended or adjusted under 35 U.S.C. 154(b) by 0 days.

(21) Appl. No.: 09/950,890

(22) Filed: Sep. 10, 2001

(51) Int. Cl.[7] ..... A01H 5/00

(52) U.S. Cl. ..... Plt./371

(58) Field of Search ..... Plt./371

*Primary Examiner*—Kent L. Bell
(74) *Attorney, Agent, or Firm*—James A. Lucas; Driggs, Lucas, Brubaker & Hogg Co., L.P.A.

(57) ABSTRACT

A Guzmania hybrid having large lavender pink floral bracts that fade to light pink. The inflorescence is very large, being 10"–12" wide and 17–18" tall making it suitable for growing in 6" containers.

1 Drawing Sheet

BOTANICAL CLASSIFICATION

*Guzmania lingulata×wittmackii.*

VARIETY DENOMINATION

'GUZ 230'.

BACKGROUND OF THE INVENTION

The present invention relates to a newly developed interspecific hybrid Guzmania plant resulting from a planned breeding program that I conduct on an ongoing basis. The objects of the breeding program include the crossing of selected parent plants from the numerous compatible species within the genus to obtain plants with novel and attractive phenotypes, coloration, and flowering forms. Other important selection factors may include ultimate plant size and shape, disease resistance, tolerance to different soil and growing conditions and vigor.

Among the objectives of my program are to produce plants of the Bromeliaceae family which will be attractive to the consumer; which will develop reasonably rapidly under controlled conditions, and which retain for a long period of time, highly attractive and bright inflorescence; i.e., bract coloration, after being induced into the flowering stage. It is a specific objective to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an objective to develop plants which may be easily and efficiently multiplied by state-of-the-art tissue culture methods while continuing the distinctive characteristics of the plants through progressive clonal generations.

The plant of this disclosure was discovered among a group of seedlings resulting from the cross of a seed parent *Guzmania lingulata* 'Panama Red Leaf' (unpatented) with a pollen parent *Guzmania wittmackii* 'Lilac Long Bracts' (unpatented). With the recognition that this seedling from the cross satisfied the objects of the breeding program, the individual was isolated and set aside for further observation and testing. The resulting selection has been assigned the designation 'GUZ 230' for purposes of identification. This plant has been reproduced by tissue culture under controlled conditions at Evergem Belgium, and the clonal specimens resulting therefrom have been determined to be identical to the original selection in all distinguishing characteristics.

The superior attributes of this plant will be revealed in the botanical descriptions to follow.

SUMMARY OF THE INVENTION

The attributes of the plant 'GUZ 230' which distinguish it from the other similar Guzmania hybrids known to me are described as follows:

The hybrid shows unique lavender pink floral bracts that fade to light pink coloration. The inflorescence is very large, being 10"–12" wide by 17"–18" tall.

The age of the observed plant is 26 months. The plant was grown under greenhouse conditions in coastal southern California. Observations were made in early afternoon in July.

This plant is compared with its parents in the following respects:

*Guzmania lingulata* 'Panama Red Leaf' is 10" tall and 30" wide with leaves 15" long and 1¼" wide, lanceolate acute in shape. Base of leaf is stained 64A abaxial and adaxial, apex of leaf is 137B adaxial and 146B abaxial. Inflorescence is 10" tall and 7.5" wide. Scape bracts are 3.5–3.75" long and 1" to 1.25" wide, color 44D adaxial and 43C abaxial. Primary bracts are 4¼ to 4½" long, 1" to 1¼" wide. Color is 42B abaxial and adaxial. Floral bracts are 1.5 to 1.75" long and 0.5" to 0.75" wide, color 42B abaxial and adaxial. Scape bracts are lanceolate acute, and the floral bracts are lanceolate acuminate.

*Guzmania wittmackii* 'Lilac Long Bracts' is 42" wide and 42" tall with leaves 26" to 28" long and 1.75 to 2" wide, lanceolate acute in shape. Foliage color is 137 B adaxial and abaxial. Inflorescence is 30" to 34" tall and 23" wide. Scape bracts are 18" to 20" long, 1.75" to 2" wide; color 64A staining to 137 B abaxial and adaxial. Primary bracts are 11" to 12" long and 1.25" to 1.5" wide, colored 67A abaxial and 67 B adaxial. Floral bracts are 5.75" to 8" long and 1" to 1.25" wide colored 71 D abaxial and adaxial. Bracts are lanceolate acute to lanceolate acuminate.

BRIEF DESCRIPTION OF THE DRAWING

The single color photograph depicts a mature plant in mid to late flowering stage. Illustrated are the mature leaves, scape bracts and primary bracts. The color definitions in the specification have been taken from The R.H.S. Colour Chart of The Royal Horticultural Society. The colors depicted are believed to be of a high level of color fidelity and are believed to be as close to the actual coloration of the plant as possible in a photographic illustration of this quality. However, due to factors such as light reflectance, cultural conditions and horticultural practices, the coloration of this plant should be understood to be approximate. For example, the bract color might slightly fade if the plant is subjected to bright light and the leaf color may vary depending on the composition and the concentration of fertilizer which may be applied to the plant.

BOTANICAL DESCRIPTION OF THE PLANT

Parentage:
- *Seed parent.*—*Guzmania lingulata* 'Panama Red Leaf'.
- *Pollen parent.*—*Guzmania wittmackii* 'Lilac Long Bracts'.

Propagation:
- *Method of asexual reproduction.*—Tissue Culture.
- *Where reproduction took place.*—BVBA DROOGTE 139, B9940 Evergem, Belgium.

Plant:
- *Type.*—Monocot perennial.
- *General characteristics.*—Medium in size Overall height from soil surface including inflorescence — 24"–26". Overall spread — 31"–34".
- *Habit.*—Form: compact.
- *Temperature tolerance.*—Not tolerant to temperatures below 43° F.
- *Resistance to disease and pests.*—Typical of the species.

Leaves:
- *Quantity.*—About 30.
- *Size.*—Large. Length: 18"–20". Width: 1.5" to 1.75" (mid length).
- *Shape.*—Lanceolate; tip acute.
- *Attitude.*—Ascending.
- *Texture.*—Smooth adaxial and abaxial.
- *Margin.*—Entire.
- *Stipules.*—None.
- *Coloration.*—New foliage — RHS 137A adaxial and RHS137C abaxial. Mature foliage — RHS 137A adaxial and RHS 137C abaxial.

Scape bracts:
- *Lower.*—Size: 9"–11" long by 1.5"–1.75" wide. Shape: lanceolate acute tip. Color: 64B at base abaxial and adaxial, staining into 147A toward tips. Texture: smooth. Margin: entire.
- *Upper.*—Size: 5" long by 1¼" wide. Shape: Lanceolate acute tip. Color: 64B adaxial and abaxial. Texture: Smooth. Margin: Entire.

Primary bracts:
- *Size.*—5"–6.5" long by 1.5"–1.75" wide.
- *Shape.*—Wide, lanceolate, acute tip.
- *Color.*—RHS 64-B abaxial and adaxial.
- *Texture.*—Smooth.
- *Margin.*—Entire.

Floral bracts:
- *Size.*—1.75"–4" in length: 0.75"–1.25" in width.
- *Shape.*—Lanceolate, acuminate tip.
- *Color.*—64B adaxial and abaxial, 64A at apex.

Bud:
- *Size.*—Medium, 2.5" in length by 1" wide.
- *Form.*—Ovoid.
- *Texture.*—Smooth.
- *Color.*—When sepals first divide: 60D. When petals begin to unfurl: 9D. At anthesis: 10D adaxial, 2D abaxial.
- *Sepals.*—Entire. Color: At base — 2D (adaxial and abaxial). At apex — 4D (adaxial and abaxial). Number: 3. Apex: Acute.
- *Calyx.*—Shape — funnel. Size — small, ¼"–⅜". Aspect — smooth.
- *Peduncle.*—Nested in foliage. Bud does not open well. Peduncle not affected by adverse conditions.

FLOWER

Blooming habit: Inflorescence a branched spike. Blooms once. Other Habit: In mature plant, full color is reached in 14 to 16 weeks. After induction, blooms at any time of year.

Inflorescence:
- *Size.*—Very large — when fully expanded 10" to 12" wide, 17"–18" inflorescence.
- *Borne.*—Singly.
- *Form.*—When first open: tubular; retains its form to the end.
- *Petalage.*—Number of petals under normal conditions: 3. Shape: Oval. Length: 1¼". Width: ¼".
- *Color.*—Center of flower (adaxial): 10D. Petals (adaxial): 10D, 4D at base, 9D at apex. Petals (abaxial): 2D, 4D at base, 9D at apex.

Petals:
- *Texture.*—Soft. Unaffected by wet or hot weather.
- *Appearance.*—Inside: Shiny. Outside: Shiny. Form: Oval.
- *Arrangement.*—Imbricate.
- *Persistence.*—Hang on and dry.
- *Fragrance.*—None.
- *Lastingness.*—On plant: short (1–2 days). As cut flower: fair (7–14 days).

Reproductive organs:
- *Stamens.*—Anthers. Size: medium — ⅛" long. Number: 5. Color — 1C. Arrangement — Regular around styles. Filaments: Threads: short — ¼". Color — 2D.
- *Pollen.*—Color — 1D.
- *Pistil.*—Number: One per flower. Styles: Loosely separated. Length — Short — 11/16". Stigmas: Color 2D. Ovaries: superior; enclosed in calyx.

Fruit: A three celled infertile capsule splitting longitudinally when mature, seeds with pappus-seeds not viable.

What is claimed is:

1. A new and distinct variety of Guzmania plant named 'GUZ 230' as illustrated and described herein.

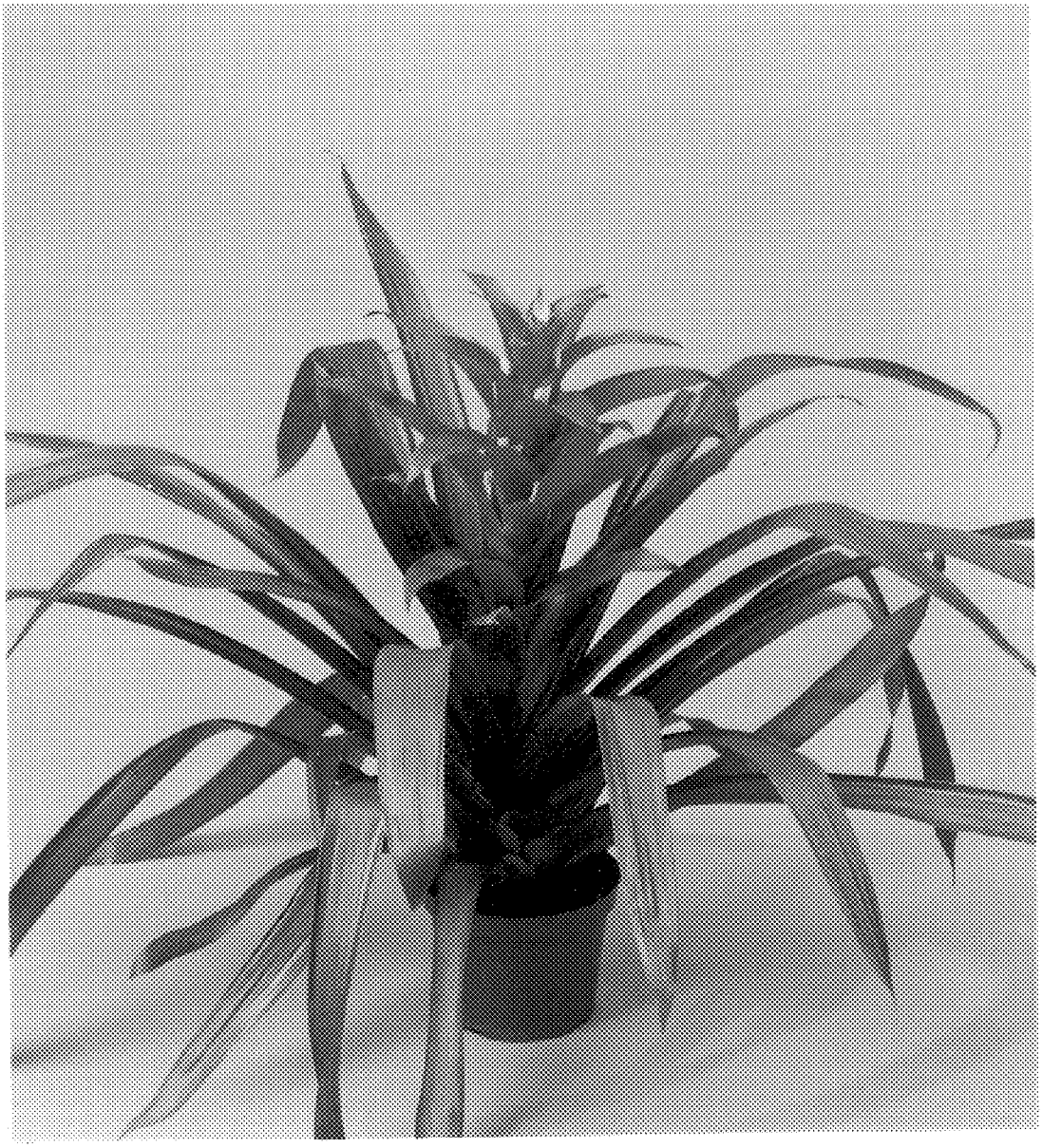

* * * * *